US010272013B2

(12) United States Patent
Chapman et al.

(10) Patent No.: US 10,272,013 B2
(45) Date of Patent: Apr. 30, 2019

(54) CPR FEEDBACK SYSTEM PROGRESSIVELY DIMINISHING TARGET COMPRESSION DEPTH TO PREVENT OVER-COMPRESSION

(71) Applicant: Physio-Control, Inc., Redmond, WA (US)

(72) Inventors: Fred William Chapman, Newcastle, WA (US); Gary Debardi, Kirkland, WA (US)

(*) Notice: Subject to any disclaimer, the term of this patent is extended or adjusted under 35 U.S.C. 154(b) by 818 days.

(21) Appl. No.: 14/552,769

(22) Filed: Nov. 25, 2014

(65) Prior Publication Data

US 2015/0257971 A1 Sep. 17, 2015

Related U.S. Application Data

(60) Provisional application No. 61/951,807, filed on Mar. 12, 2014.

(51) Int. Cl.
*A61H 31/00* (2006.01)
*A61N 1/39* (2006.01)

(52) U.S. Cl.
CPC .......... *A61H 31/00* (2013.01); *A61H 31/005* (2013.01); *A61H 2201/1253* (2013.01); *A61H 2201/5061* (2013.01); *A61H 2201/5064* (2013.01); *A61H 2203/0443* (2013.01); *A61N 1/39* (2013.01)

(58) Field of Classification Search
CPC .................. A61H 31/00; A61H 31/005; A61H 2201/5061; A61H 2203/0443; A61H 2201/1253; A61H 2201/5064; A61H 31/004; A61H 31/007; A61H 31/008; A61H 2201/0107; A61H 2201/0157; A61H 2201/1619; A61H 2201/1664; A61H 2201/5058; A61H 2201/5079; A61H 2201/5084; A61H 2203/0456; A61H 2205/084; A61N 1/39
See application file for complete search history.

(56) References Cited

U.S. PATENT DOCUMENTS

| 2006/0173500 | A1* | 8/2006 | Walker | A61B 5/046 607/5 |
| 2006/0229680 | A1* | 10/2006 | Chapman | A61N 1/39 607/5 |
| 2008/0300517 | A1* | 12/2008 | Nysaether | A61H 31/005 601/41 |

(Continued)

*Primary Examiner* — Quang D Thanh
(74) *Attorney, Agent, or Firm* — Miller Nash Graham & Dunn LLP

(57) ABSTRACT

A CPR feedback system, software and methods are provided. A top height sensor can be used to track the height of the patient's chest during the CPR chest compressions, by detecting a top aspect of its location. A depth module may generate, from a detected top aspect, a depth value for a depth reached by a current compression. A counter may determine a compressions number, e.g. for the current compression. A memory may store a depth variable that can return different target values for the target depths of individual compressions. A user interface has an output device that may output an indication for the rescuer, which reflects how well the depth value of the current compression matched a corresponding target value for it. The target values may be set so as to follow a preset profile, or change according to optional measurements of force and other parameters.

19 Claims, 14 Drawing Sheets

GUIDING CPR CHEST COMPRESSIONS
TO DIMINISHING TARGET DEPTH
FOR THE SESSION

(56) References Cited

U.S. PATENT DOCUMENTS

| | | |
|---|---|---|
| 2010/0185127 A1 | 7/2010 | Nilsson et al. |
| 2010/0228165 A1 | 9/2010 | Centen |
| 2011/0301511 A1 | 12/2011 | Freeman |
| 2012/0010543 A1* | 1/2012 | Johnson ............... A61N 1/3925 601/41 |
| 2013/0225972 A1* | 8/2013 | Banville ............. A61H 31/005 600/409 |
| 2014/0257150 A1* | 9/2014 | Totman ............... A61H 31/005 601/41 |

* cited by examiner

FIG. 4            *USER INTERFACE*

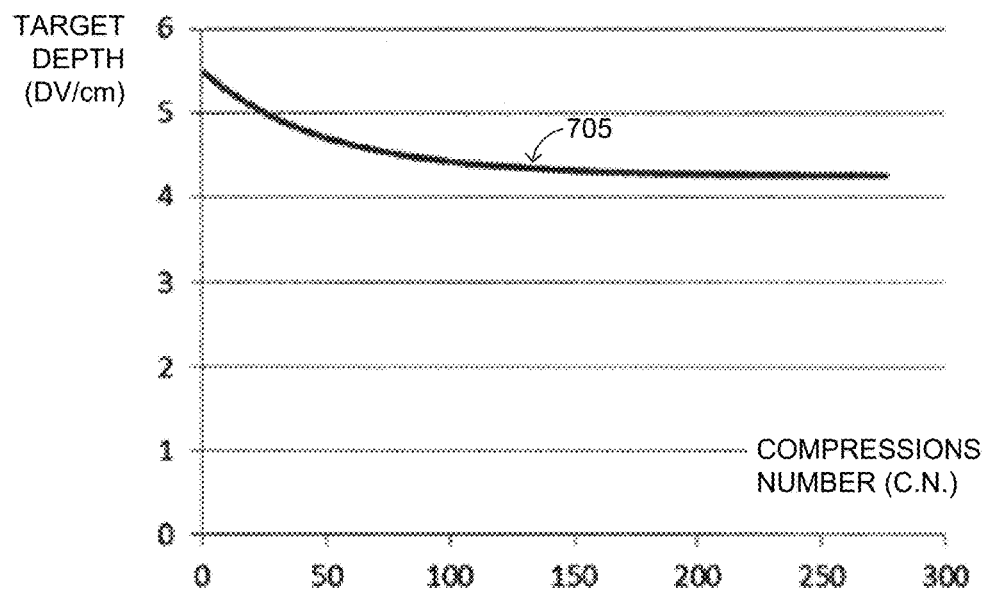
FIG. 7   SAMPLE PROFILE
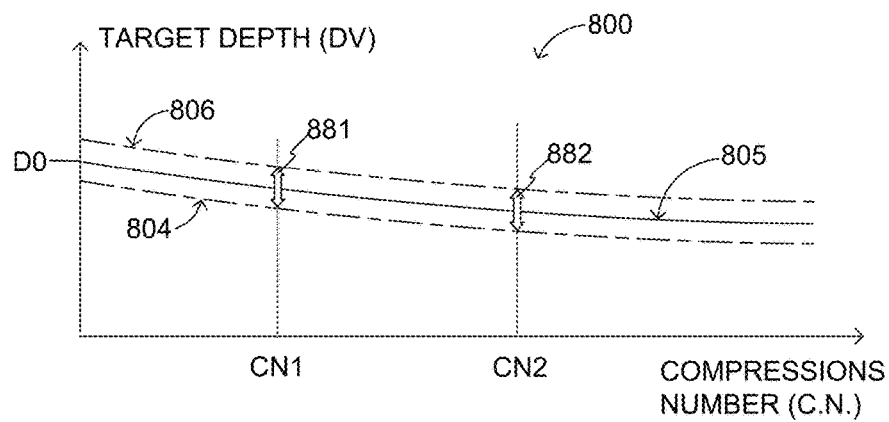
FIG. 8   TARGET DEPTH PART OF TARGET RANGE

| COMPRESSIONS NUMBER (C.N.) | TARGET VALUE FOR DEPTH VARIABLE DV |
|---|---|
| 0 | 5.5 |
| 1 | 5.48 |
| 2 | 5.45 |
| 3 | 5.43 |
| 4 | 5.40 |
| 5 | 5.38 |
| ... | ... |

*PORTION OF LOOK-UP TABLE IN MEMORY*

FIG. 9

$$DV = D0 - DR*F*[1 - e**(-(C.N.)/CNB)]$$

*SAMPLE PROFILE COMPUTATION FOR TARGET DEPTH*

FIG. 10

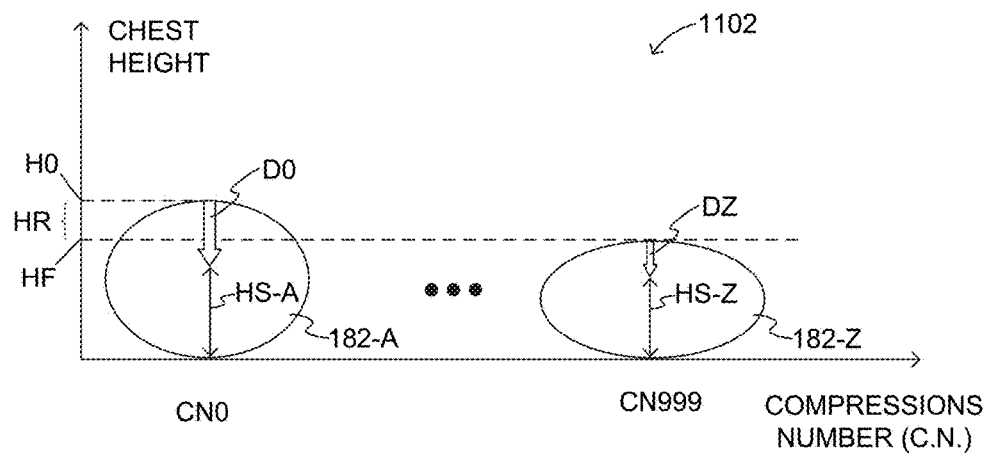
FIG. 11  *INITIAL & FINAL DIMENSIONS*
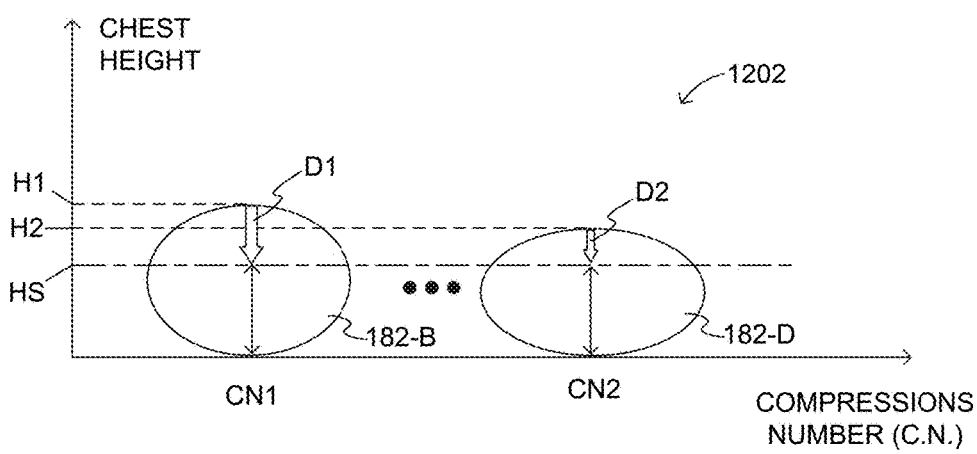
FIG. 12  *COMPRESSIONS TO MAINTAIN HEIGHT*

*DETECTING APPLIED FORCE*

BRIEF POWER LOSS EVENT

FIG. 17 — DISPLAY WITH SHIFTING TARGET DEPTH

CPR FEEDBACK SYSTEM PROGRESSIVELY DIMINISHING TARGET COMPRESSION DEPTH TO PREVENT OVER-COMPRESSION

CROSS REFERENCE TO RELATED PATENT APPLICATIONS

This patent application claims priority from U.S. Provisional Patent Application Ser. No. 61/951,807, filed on Mar. 12, 2014, the disclosure of which is hereby incorporated by reference for all purposes.

BACKGROUND

In humans, the heart beats to sustain life. In normal operation, the heart pumps blood through the various parts of the body. Sometimes the heart malfunctions, in which case it can beat irregularly, or not at all. The cardiac rhythm is then generally called an arrhythmia. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively and, if not treated, death can occur. In fact, the American Heart Association (AHA) reported in 2014 that SCA results in more than 500,000 deaths per year in the United States alone. Further, a SCA may result from a condition other than an arrhythmia. One type of arrhythmia associated with SCA is known as Ventricular Fibrillation (VF). VF is a type of heart malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes, the rate of survival for SCA victims averages less than 2%.

During VF, the person's condition deteriorates, because blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for patients with some kinds of non-VF cardiac arrest, such as asystole and Pulseless Electrical Activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved.

It is not easy for humans to perform good CPR chest compressions. It is hard for a rescuer to continue gauging the compression depth that should be reached from their position. If the depth is not adequate, then it might not cause enough blood flow. If the depth is too much, it might cause damage. CPR feedback systems have been developed to coach and guide the delivery of CPR chest compressions.

Another challenge is that, due to the repeated CPR chest compression, the chest of the patient progressively breaks down, and the chest resting height is thus gradually diminished. The process of breaking down may be progressive, even when good CPR compressions are being performed. The process could also be sudden, for example in the instances when ribs break.

BRIEF SUMMARY

The present description gives instances of CPR feedback systems, software and methods, the use of which by a rescuer may help overcome problems and limitations of the prior art.

A CPR feedback system, software and methods are provided. A top height sensor can be used to track the height of the patient's chest during the CPR chest compressions, by detecting a top aspect of its location. A depth module may generate, from the detected top aspect, a depth value for a depth reached by a current compression. A counter may determine a compressions number, e.g. for the current compression. A memory may store a depth variable that can return different target values for the target depths of individual compressions. A user interface has an output device that may output an indication for the rescuer, which reflects how well the depth value of the current compression matched a corresponding target value for it. The target values may be set so as to follow a preset profile, or change according to optional measurements of force and other parameters.

An advantage over the prior art is that that rescuer can be guided to adjust the compression depth according to the changing patient's body at the time. As the chest progressively breaks down, the depth of the compressions can be adjusted so as to prevent injury to important organs and/or blood vessels.

These and other features and advantages of this description will become more readily apparent from the Detailed Description, which proceeds with reference to the associated drawings in which:

BRIEF DESCRIPTION OF THE DRAWINGS

FIGS. 5-7 show sample profiles of gradually diminishing chest compression depths according to embodiments.

FIG. 8 is a diagram showing how a sample profile can be part of a target range according to embodiments.

FIG. 9 is a portion of a sample lookup table in a memory for implementing the profile of FIG. 7 according to embodiments.

FIG. 10 is a sample equation for computing a profile such as the profile of FIG. 7 according to embodiments.

FIG. 11 is a diagram for illustrating salient dimensions in planning the changing depth of compressions according to embodiments.

FIG. 12 is a diagram for illustrating how the changing depth of compressions may be planned according to sample embodiments.

DETAILED DESCRIPTION

As has been mentioned, the present description is about CPR feedback systems, software and methods. Embodiments are now described in more detail.

Figure 1:
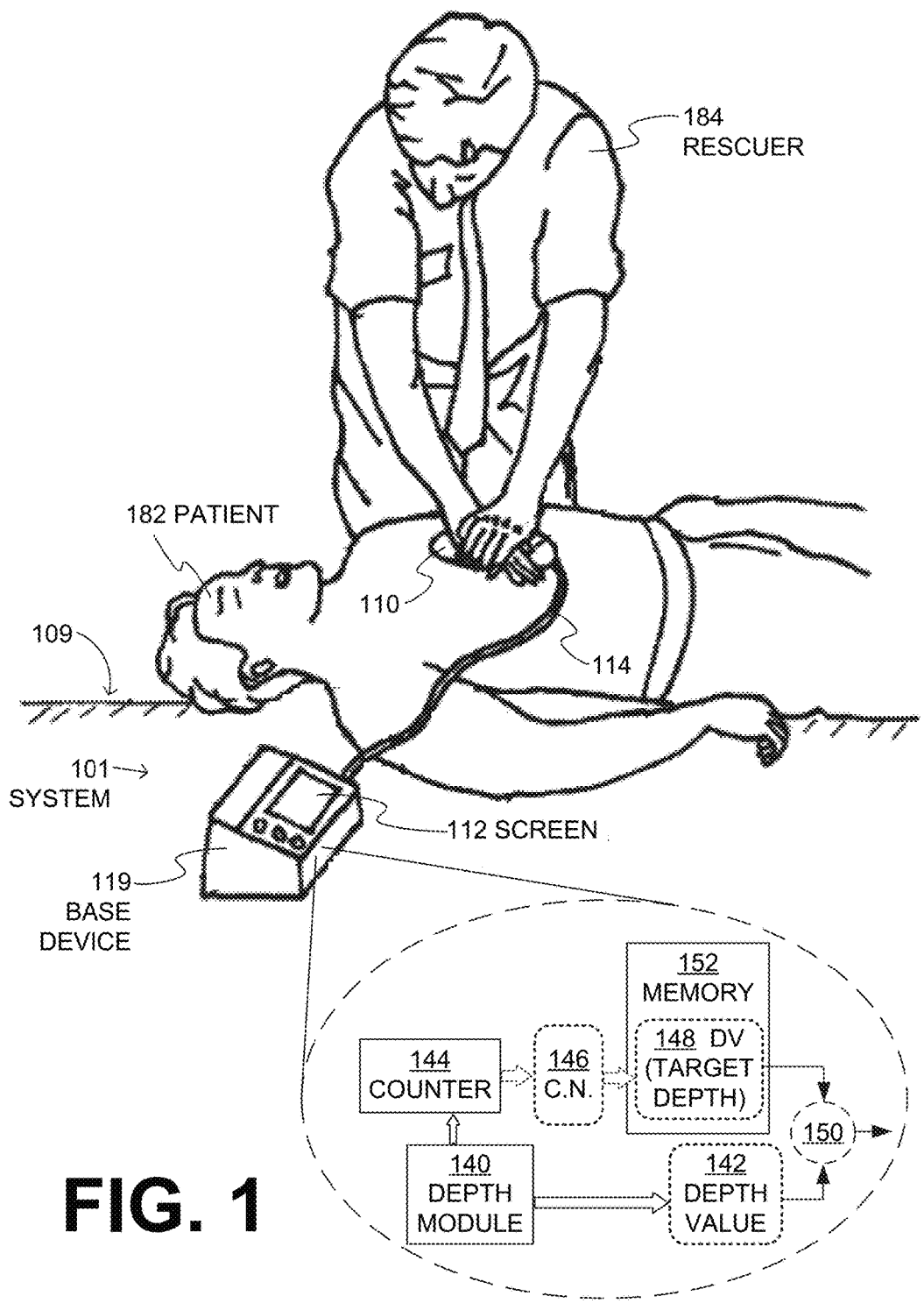
FIG. 1 is a diagram of a scene where a rescuer is performing chest compressions on a patient using a CPR feedback system according to embodiments, and in which sample components of the system are also shown.

FIG. 1 is a diagram of a scene during a session where a rescuer 184 is performing sequential Cardio-Pulmonary Resuscitation ("CPR") compressions on the chest of a patient 182 who is lying on ground 109. Rescuer 184 is also using a sample system 101, which is made according to embodiments. Particular system 101 is for real time CPR feedback, but that need not be the case according to embodiments—it might have uses in addition or in lieu of CPR feedback.

A CPR feedback system according to embodiments, such as system 101, may include a top height sensor. The top height sensor could be configured to be maintained at a substantially fixed vertical relationship with respect to a top of the patient's chest while the compressions are being performed. This may be accomplished in a number of ways. For example, the top height sensor can be configured to be placed on the patient's chest, as shown in the example of FIG. 1, where a top height sensor 110 is placed on the chest of patient 182 and is thus squeezed by rescuer 184 during each compression. Alternately, the top height sensor can be configured to be coupled to an arm or a hand of the rescuer who performs the chest compressions.

In embodiments, a top aspect of the top height sensor's location may be detected by the system. This may be accomplished in a number of ways. For example, the top aspect can be the sensor's location itself, or a time rate of change of the location (such as the sensor's speed), or a time rate of change of a time rate of change of the location (such as the sensor's acceleration). The top height sensor may be implemented as is known in the art. For example, it could use one or more magnets, one or more electromagnets, an accelerometer, optical devices, etc.

In the example of FIG. 1, system 101 also includes a base device 119, although that is not necessary for embodiments. Base device 119 may be operatively coupled with top height sensor 110. In the example of FIG. 1, coupling with top height sensor 110 is by a wire 114, although coupling may be wireless, such as magnetic, electromagnetic, and so on.

A CPR feedback system according to embodiments, such as system 101, may also include a depth module. In the example of FIG. 1, a depth module 140 is implemented in base device 119.

The depth module can be configured to generate a depth value from the top aspect detected by the top height sensor, and may be considered to correspond substantially closely to the amount that the chest of the patient is compressed by the current compression. The depth value can be related to a detected depth reached by a certain compression, a group of compressions, a current compression, or a group of compressions that includes the current compression. The latest depth value could thus be of the current compression, which may be the latest one that was counted, or a group of compressions. In the example of FIG. 1, a depth value 142 is shown.

In some embodiments, a CPR feedback system may also include a bottom height sensor, an example of which is not shown in FIG. 1. More particularly, the patient could be lying on a support surface such as the floor. In the example of FIG. 1, the support surface would thus be ground 109. In other instances, the support surface can be a bed or a gurney that is flexible and might move downwards as a result of the compressions; this downward movement could make the measurement of the top height sensor less reliable as a way of detecting how much the patient's chest was actually compressed. The bottom height sensor can help correct for that by providing another reference point. More particularly, the bottom height sensor can be configured to be maintained at a substantially fixed vertical relationship with respect to the support surface while the compressions are being performed, for example by being placed under the patient. From that position, the bottom height sensor can be configured to detect a bottom aspect of its own location. In such embodiments, the depth value can be generated also from the detected bottom aspect.

A CPR feedback system according to embodiments, such as system 101, may also include a counter. In the example of FIG. 1, a counter 144 is implemented in base device 119.

The counter can be configured to determine a compressions number ("C.N.") that is related to a number of the compressions that have been performed during the session. The C.N. can be determined at least from the top aspect detected by the top height sensor. In some embodiments, the C.N. can be determined from an output of the depth module, which in turn is determined from the top aspect detected by the top height sensor. In some embodiments, the C.N. is determined by counting the compressions in the session. Accordingly, the C.N. can have a value of CURRENT_CN for the current compression, which may be the latest one that was counted. In the example of FIG. 1, a compressions number 146 is indicated.

A CPR feedback system according to embodiments, such as system 101, may also include a memory. The memory can be configured to store a depth variable DV that represents a target depth for the compressions. In the example of FIG. 1, a memory 152 is implemented in base device 119. A depth variable DV 148 is shown, which is further labeled by what it represents.

A CPR feedback system according to embodiments may guide and coach the rescuer to perform chest compressions whose depth is variable. This depth can be considered the target depth from the point of view of the system. This target depth may depend on how many compressions have been performed so far, among other factors. In other words, this target depth may depend on the compressions number determined by the counter. Accordingly, the depth variable can be configured to return a target value that depends on the determined C.N. Before completing the description of FIG. 1, possible target values are now described in more detail.

Figure 2:
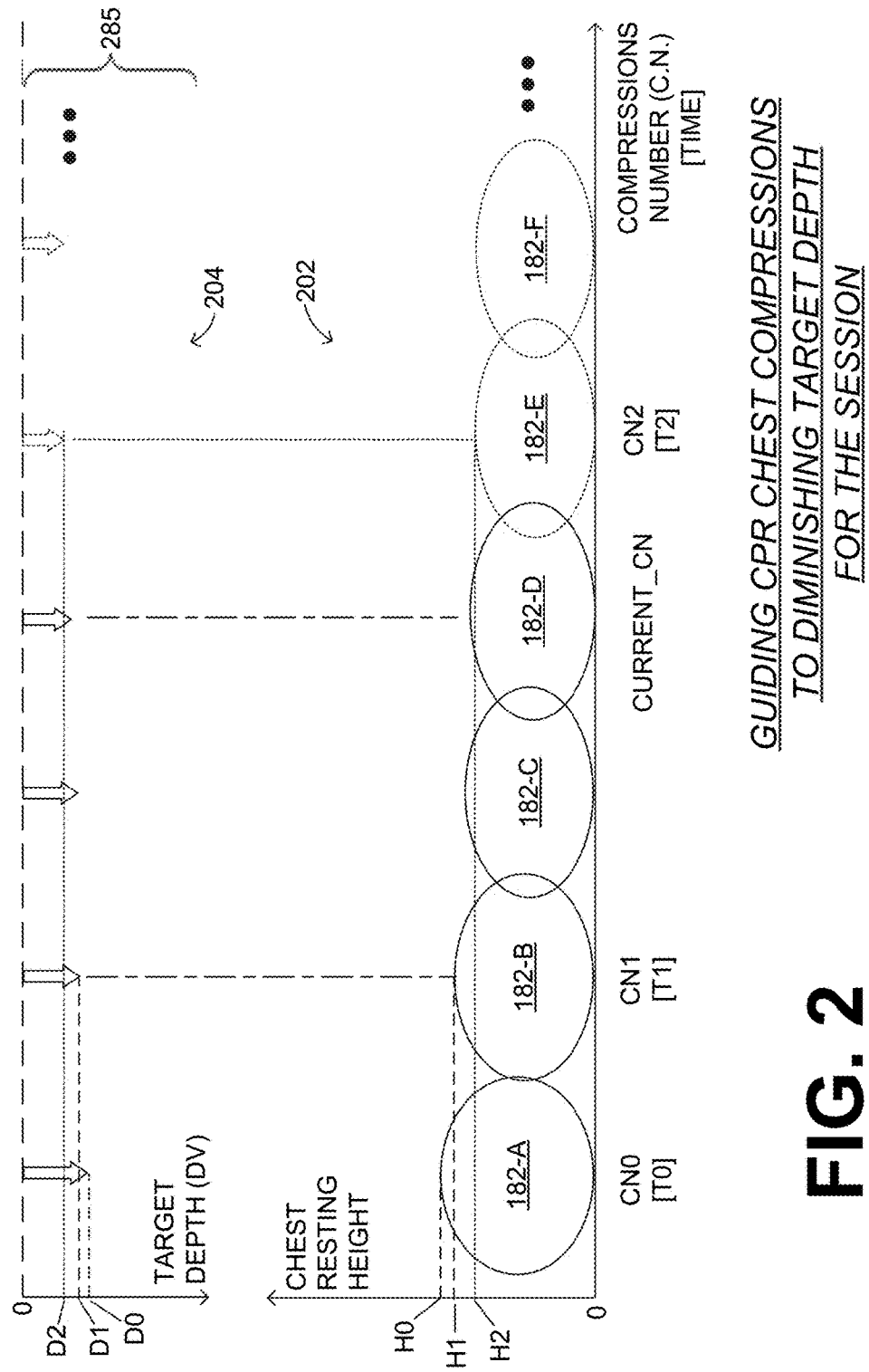
FIG. 2 shows two time diagrams during a session of a patient receiving CPR chest compressions by a rescuer who uses a CPR feedback system according to embodiments, and which illustrate that due to compressions the chest resting height decreases and that sample subsequent compressions are guided by feedback to be accordingly not as deep.

FIG. 2 shows two time diagrams 202, 204 that represent what may happen during a session of a patient receiving CPR chest compressions by a rescuer who uses a CPR feedback system according to embodiments. Diagrams 202 and 204 share a common horizontal axis for the compressions number C.N. for the session. In this axis particular sample values are shown. These include CN0 (start of the session), and CURRENT_CN for the current value of the C.N. Another value is CN1, which is a first C.N. that can be considered for purposes of making the explanations of this document clearer. The most frequent values of CN1 are from CN0 to CURRENT_CN. One more shown value is CN2, which is a second C.N. that can be considered, and whose frequent values range from CURRENT_CN to a value larger than CN1 by at most 100.

It will be understood that the horizontal axis does also, in some way, represent the time of the session. Accordingly, CN0, CN1, CN2 correspond to times T0 (start of session), T1 (when C.N.=CN1), and T2 (when C.N.=CN2), respectively.

Diagram 202 also shows views 182-A, 182-B, 182-C, 182-D, 182-E, 182-F, of a cross-section of the patient's torso, for selected values of the horizontal axis, some of which were mentioned above.

In diagram 202 there is also a vertical axis for the resting height of the chest. The vertical axis is perpendicular to the horizontal axis. In such cases it is customary to have the two axes intersect where they both have the "zero" value, but this is not done in FIG. 2 so as to not unnecessarily clutter the drawing.

In diagram 202 it will be observed that, at the start of the session (CN0, time T0), the chest resting height is at a value H0. Then, at CN1 (time T1), the chest resting height is at a value H1, which is less than H0. Then, at CN2 (time T2), the chest resting height is at a value H2, which is less than H1. At even more compressions, torso view 182-F may have an even lower chest resting height (not specifically indicated in FIG. 2). As CPR chest compressions are performed, the chest resting height diminishes because the repeated compressions alter the mechanics of the thorax. More particularly, the chest breaks down over time, and its mechanical properties and dimensions change. In the example of FIG. 2, the chest height of the torso changes gradually, but this is not the only case that is anticipated by embodiments.

Diagram 202 depicts the chest resting height. It will be understood by a person skilled in the art that the exact chest resting height may or may not be known. Even when it is not known, the learned top aspect of the location of the top height sensor can help determine a working height that can be considered to be the chest resting height. This learned top aspect may be confirmed by detecting after an individual compression, a release by the rescuer. The release can be detected, for example, by a force detection module. The working height may then exhibit the same evolution during the session as shown in diagram 202.

Diagram 204 depicts target depths 285 according to embodiments. These target depths are depicted considering the same horizontal axis as diagram 202, and along a vertical axis whose values increase in the downward direction. These target depths are implemented by depth variable DV, and so the vertical axis indicates target values of depth variable DV. It will be observed that, at the start of the session (CN0, time T0), the target value is a value D0. Then, for one of the compressions numbers CN1 (time T1), the target value is a first value D1, which is less than D0. For the C.N. that corresponds to the current compression, the target value can be a current value (not indicated). For another one of the C.N.s CN2 (time T2), the target value is a second value D2, which is at least 4% smaller than the first value D1. At an even higher C.N., the target value may be even less (not indicated explicitly in FIG. 2).

In diagram 204, it will be observed that the target value diminishes, i.e. is reduced, as the session progresses and the C.N. increases. In other words, subsequent compressions are guided by feedback to be not as deep as the initial compressions, so as to compensate for the gradual chest reduction of diagram 202. Ways to implement this reduction according to embodiments are described later in this document.

Returning to FIG. 1, a CPR feedback system according to embodiments, such as system 101, may also include a user interface. The user interface may be implemented in any way known in the art for being used by the rescuer. In embodiments, the user interface has an output device that is configured to output an indication that is perceptible by the rescuer. The output device can be implemented in any number of ways. In some embodiments, the output device is such that the indication is audible, for example it includes a speaker, etc. The indication may then include tones, alarms, verbally made comments and commands, etc. In some embodiments, the output device is such that the indication is visible, for example it may include lights, a screen, etc. In the example of FIG. 1, the output device includes a screen 112 implemented in base device 119. The indication may then be graphs, images, etc.

The indication of the output device may be output responsive to the depth value generated by the depth module. This indication may reflect how well the rescuer is adhering to the coaching. More particularly, this indication may reflect how well the depth value of the detected depth of the current compression matches the target value returned by the depth variable for the current compression. In the example of FIG. 1, a comparison reflected by the indication is shown symbolically by an optional subtracting device 150, which compares depth value 142 and depth variable 148. Rescuer 184 may use this indication to adjust the depth of the CPR compressions he is performing.

As mentioned above, a CPR feedback system according to embodiments, such as system 101, need not be dedicated to being only a CPR feedback system. Rather, it could be part of a monitor-defibrillator, in which case the system has correspondingly additional capabilities. For example, the system may also include a defibrillation module that is configured to defibrillate the patient, if need be.

Figure 3:
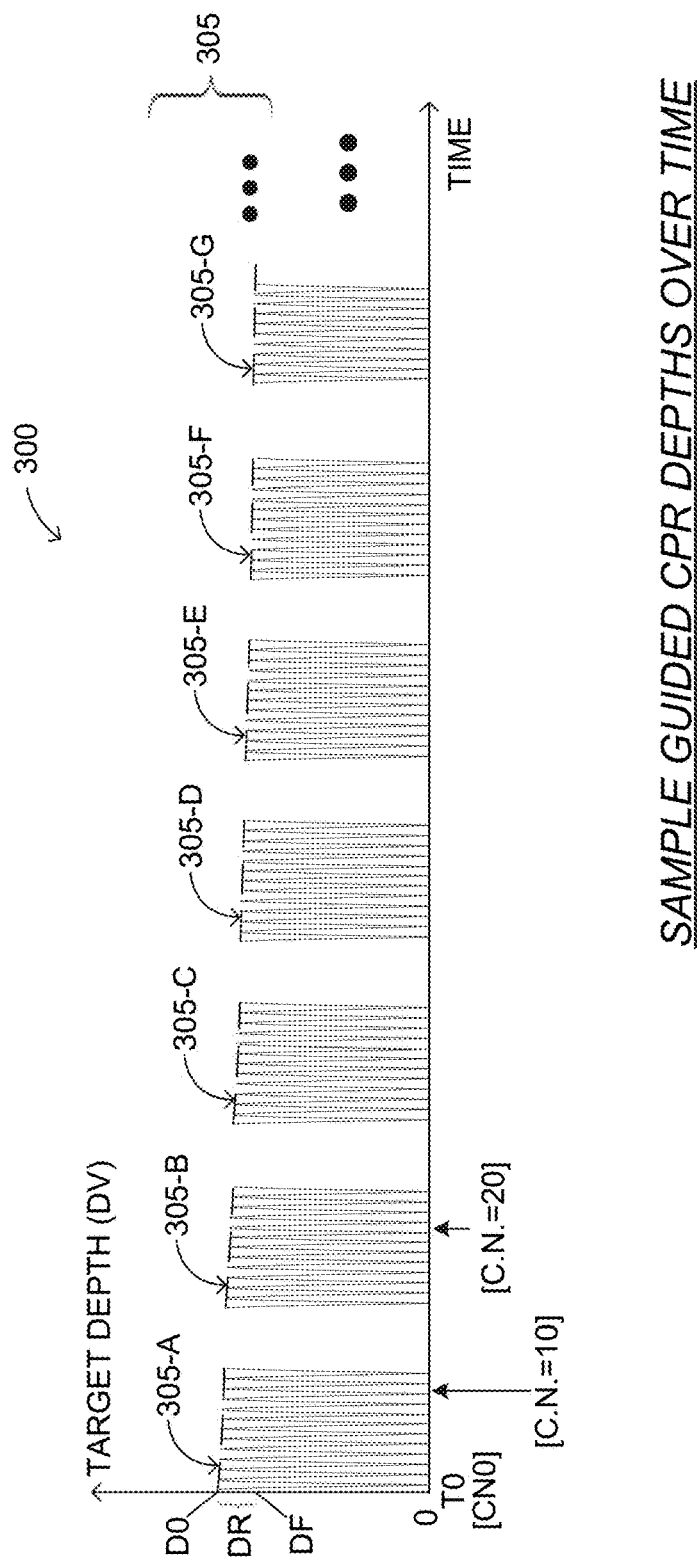
FIG. 3 is a time diagram of gradually diminishing depths of sample chest compressions that are guided by feedback in a session according to embodiments.

FIG. 3 is a diagram 300 which, in the horizontal axis, shows time for a session of performing CPR compressions. In the vertical axis diagram 300 plots the target depth of sample chest compressions that are guided by feedback according to embodiments. The compressions are shown in groups of 12, as in some resuscitation protocols, although different size groups are possible. Compressions numbers are indicated for the C.N. being 10 and 20.

In diagram 300, the compressions are shown as sequential pairings of downward-going compressions followed by upward-going releases. This could be, for example, an approximate waveform output that some embodiments of the depth module could generate. The lowest point would be the depth value that is related to the maximum detected depth that is reached during the travel of the compression. In diagram 300, the reached detected depths are shown artificially aligned at the horizontal axis, so that the depths can be compared to each other as heights on the vertical axis. This comparison is enabled regardless of the exact height that each compression started from, or the exact depth it reached within the patient's body, in an absolute elevation sense.

By comparing the depths on the vertical axis, therefore, it will be observed that the targeted compressions have a starting depth of D0 at T0 (CN0). The compressions generally decline in depth. In the example of FIG. 3, there are profiles 305-A, 305-B, 305-C, 305-D, 305-E, 305-F, 305-G, of the compression depths, which decline within each group of the compressions, although that is not necessary; instead, each compressions group could have the same target depth. In the example of FIG. 3, the compression point at the end of a compressions group is the starting point at the beginning of the next compressions group, although that is not necessary; instead, each compressions group could start at a different value. The totality of these profiles creates a single profile 305 for the session. Both the starting depth of D0 and the profile can be implemented in a number of different ways according to embodiments. The starting depth is discussed first.

In some embodiments, the starting value is stored in the memory. More particularly, a default starting depth value can be stored in the memory. In such embodiments, an initial value can be determined from this default starting depth value. The target value can be this initial number for small value of the compressions number, e.g. before the compressions number becomes, say, 4.

In some embodiments, the starting value is entered into the system one in way or another by a user such as the rescuer. Embodiments are now described.

The user interface of the system may also have an input device. The input device may be implemented in any number of ways known for medical devices that are useable in the field, for example by including touchscreens, buttons, knobs, keys, actuators, remote interfaces of smart mobile communication devices, and so on.

The input device of a user interface according to embodiments can be configured to receive a reset input. In such embodiments, the target value can become an initial value responsive to the reset input being received. An example is now described.

Figure 4:
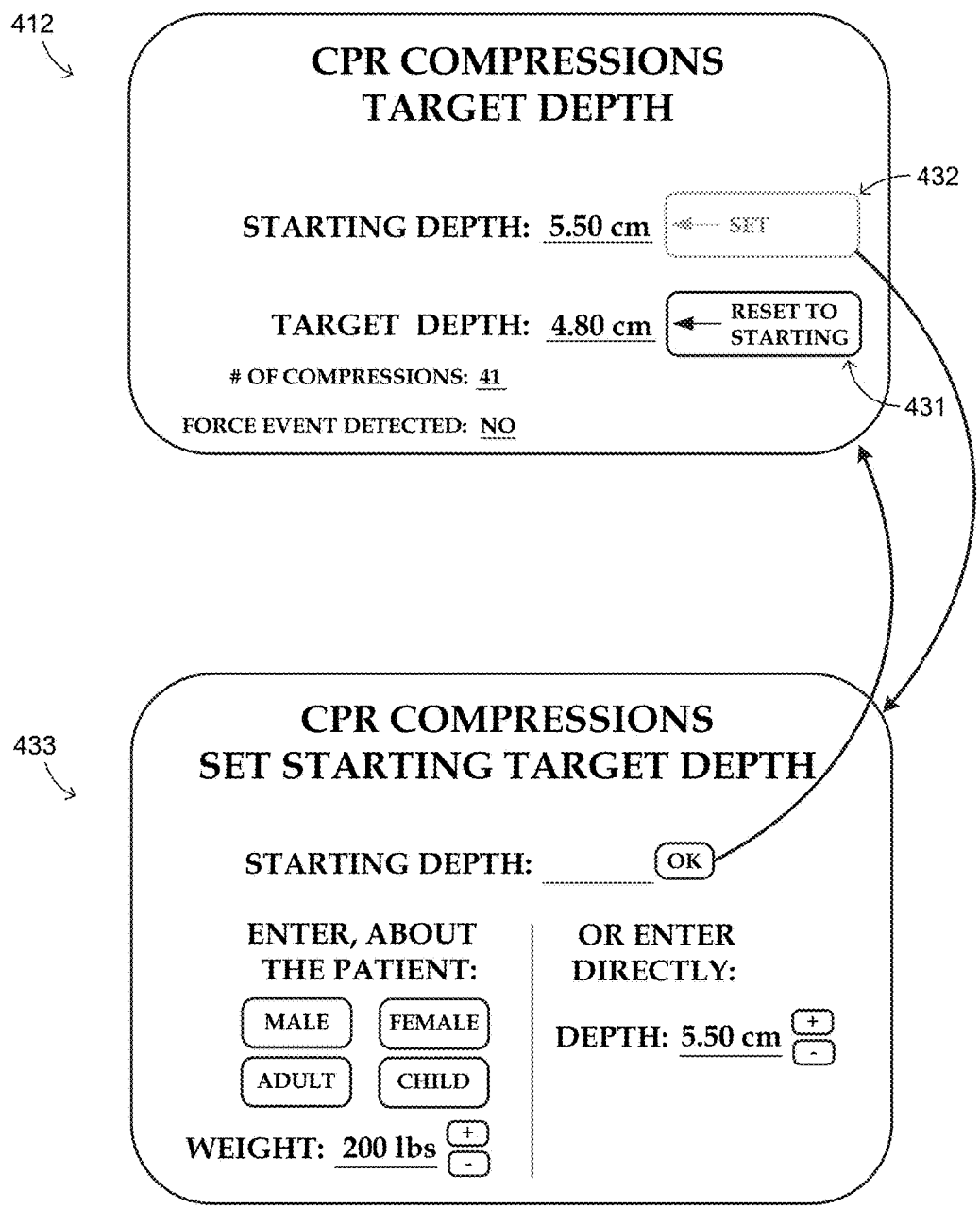
FIG. 4 is a diagram of sample screens in user interfaces of a CPR feedback system that guides a rescuer to perform CPR chest compressions of diminishing depth according to embodiments.

FIG. 4 shows a sample screen 412 of a user interface according to embodiments, which presents the information and instructions. Screen 412 could be part of what is displayed in a touch screen. Alternately, what is shown in screen 412 could be real buttons, displays, etc. According to screen 412, the starting depth had been 5.50 cm, which is somewhat larger than the minimum recommendation of 5 cm of the current AHA guidelines, and also half-way within the range of 5 cm to 6 cm that is recommended by the current guidelines of the European Resuscitation Council. (For units of cm, perhaps only one decimal will suffice.) The number of compressions that have been counted is 41, and no force event has been detected. The target depth is 4.80 cm. This target depth can be the depth of the current compression that was just counted, or the expected depth of the next compression. Screen 412 shows a reset switch 431, which can be configured to receive a reset input by being pressed. If it is pressed, the current depth can be reset to the shown starting depth.

In some embodiments, the input device can be configured to receive a user input. In such embodiments, responsive to this user input being received, the target value can become a value that is determined from this user input. An example is now described.

FIG. 4 also shows a sample screen 433 according to embodiments. Screen 433 presents the information and instructions shown, and is intended to permit the user to enter a starting depth. Within the interface, screen 433 can reached in a number of ways, including by pressing a button 432 in screen 412. In the latter case, the starting depth should be entered before the compressions start. (Button 432 is shown faded in screen 412, because the compressions have already started.)

In screen 433, the user is presented with two main options. In the left-hand side, the user may enter some characteristics about the patient, and allow the system to propose a starting depth. In the right-hand side, the user may enter directly the desired depth. Either way, the top indication shows the computed or entered starting depth; when that indication reads as desired, the user may press the "OK" button to be transferred back to screen 412.

Returning to FIG. 3, the targeted compressions have a starting depth of D0 at T0 (CN0), which declines according to a profile 305. In the example of FIG. 3, in the very long term the targeted compressions may reach a final depth DF, which may represent the situation that the patient's chest has broken down as much as it would. The final depth DF could be reduced from the initial depth D0 by a reduction DR.

Returning to FIG. 2, as mentioned, the target value of depth variable DV may depend at least on the compressions number. In particular, the second value, which is the target value of the depth variable when C.N.=CN2, can be determined at least in part from a preset profile that depends on the determined C.N. FIG. 3 showed such a sample profile 305, which can be approximate because it is plotted in units of time.

Figure 5:
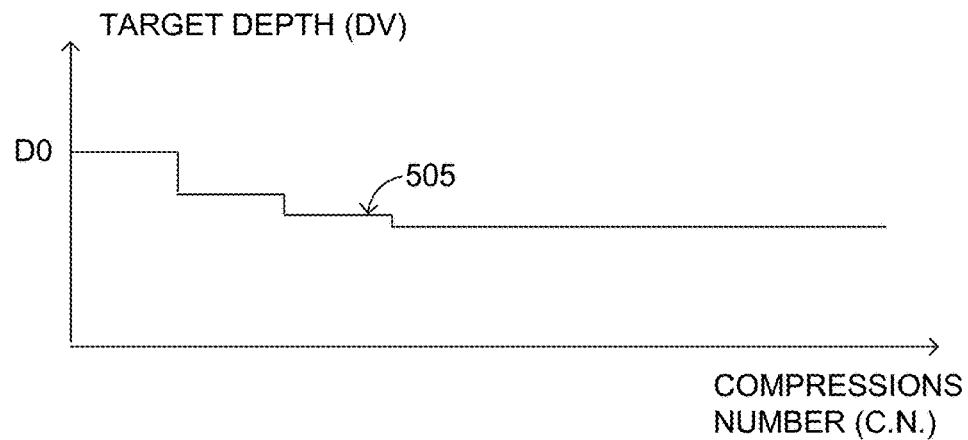
Figure 6:
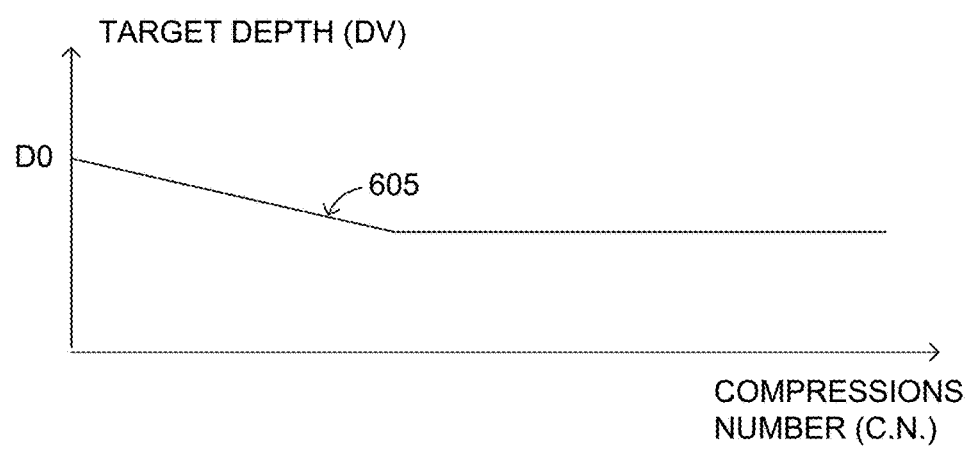

FIGS. 5-7 show sample profiles 505, 605, 705 according to embodiments, plotted against the compressions number CN. They all diminish to a final value: profile 505 according to a few steps, profile 605 according to a ramp, and profile 705 according to a declining exponential function. In such profiles the target value diminishes with increasing compressions number. For example, the target value can have an initial value before the C.N. becomes 4, and after the C.N. becomes a number over 30 the target value can be a later value that equals approximately 80% of the initial value.

While these sample profiles decline monotonically, this need not be the case for all embodiments. While these sample profiles settle to a value, this need not be the case for all embodiments. Moreover, such profiles can be default profiles, assuming nothing changes during the session. This need not be always the case, however. For example, the rescuer may change parameters during the session. Or the situation may change during an event, for instance a force event that could be detected as is described later in this document.

In some embodiments, instead of a single target value, a target range is understood. The target range could be changing according to the compressions number. For instance, the first value, which is the target value of the depth variable when C.N.=CN1, could be within a first target range. In such embodiments, the second value can be within a second target range that is different from the first target range. An example is now described.

FIG. 8 is a diagram 800 that shows how a sample profile can be part of a sample target range according to embodiments. In diagram 800, the sample target range is defined for a given compressions number as having a) a minimum value given by minimum profile 804, and b) a maximum value given by maximum profile 806. Accordingly, for C.N.=CN1 the range could be as shown by arrow 881, and for C.N.=CN2 the range could be as shown by arrow 882, which is different from arrow 881. A profile 805 could be between the minimum profile 804 and the maximum profile 806 as shown, or it could be profile 804 or profile 806, etc.

Implementing the profiles may require the depth variable to return different target values for different C.N.s. In some embodiments, such target values are stored in the memory. For example, as seen in FIG. 9, a look-up table can store different compressions numbers and corresponding target values. These target values, then, may include the first value and the second value, which correspond to C.N.s CN1 and CN2 respectively. Moreover, the target values of FIG. 9 are the ones that were used for implementing profile 705 of FIG. 7.

In some embodiments the target values are computed. More particularly, a CPR feedback system according to embodiments, such as system 101, may also include a processor. If a base device is provided, such as base device 119 in FIG. 1, then the processor may be provided within the base device.

The processor can be configured to compute the target values, such as the above-mentioned second value for the target value. Computation may happen by using equations or other known ways.

FIG. 10 is a sample equation 1005 for computing a profile such as the profile of FIG. 7, where:

DV is the targeted compression depth for a certain compressions number;

D0 is the initial target compression depth;

DR is the maximum planned reduction from the initial compression depth D0;

F is an adjustment factor;

(C.N.) is the value of the compressions number; and

CNB is a base number that controls how quickly the depth is reduced as compressions proceed (for example, at CNB compressions, $D=D_0-0.63DR$).

Profile 705 of FIG. 7 has been computed from equation 1005 by setting D0=5.5 cm, DR=1.25 cm, F=1 and CNB=50.

In some embodiments, the user may set or adjust the profile or both. For instance, the user interface may have the aforementioned input device that is configured to receive a user input. For example, a screen may be produced that gives options, similarly with how the screens of FIG. 4 permit selecting the starting depth (D0).

For adjusting the profile, the options may include choice of a profile, such as profiles 505, 605, 1005 or no changing profile at all. The profile, and its parameters, may be chosen in terms of the extent to which the chest is expected break down during compressions, or detected to do so. The choices may be made according to intended trade-offs between compressing more deeply for better blood flow, and less deeply in order to not cause injury to important organs and/or blood vessels from compressions that will progressively reach deeper and deeper, as the chest gradually breaks down.

For the chosen profile, parameters may be permitted to be chosen, such as the step sizes of profile 505, the slope of profile 605, or values DR, F, and CNB for equation 1005. In these cases the profile will depend on the compressions number, and can become adjusted responsive to the received user input. Accordingly, target values such as the above-mentioned second value can be determined at least in part from the profile that will have been thus adjusted. For example, the value of DR in equation 1005 can be based on the initial chest height, preferably if the latter can be measured without special maneuvers by the rescuer.

Moreover, the value of CNB in equation 1005 can be adjusted judiciously. For example, patient descriptors could indicate how fast the chest would break down. One would be age; the thorax of the older patient would likely break down more quickly and thus benefit from a more rapid decrease in target depth; accordingly, a smaller CNB may be used. It may be that the same would be true for gender: a female perhaps would benefit from a more rapid decrease in depth, in which case a smaller CNB may be used.

FIG. 11 is a diagram 1102 for illustrating salient dimensions in planning the changing depth of compressions according to embodiments. FIG. 11 resembles somewhat FIG. 2 in that the horizontal axis denotes the compressions number (C.N.), and torso view 182-A is shown again for CN0. Another compressions number CN999 is also shown for what could be a very large C.N., by which time the torso may have completed its breaking down process, and might appear as torso view 182-Z. As in FIG. 2, there is no implication that the patient is lying on a surface that remains static during the compressions.

In FIG. 11, the vertical axis represents chest height for torso views 182-A, 182-Z, which are H0, HF respectively. The reduction in height during the rescue session will have been HR=H0−HF.

In addition, FIG. 11 also shows compression depths D0, DZ for compressions numbers CN0, CN999, superimposed on torso views 182-A, 182-Z, respectively. In general, compression depths D0, DZ are not the same.

FIG. 11 further indicates an additional quantity, namely the part of the torso that is not displaced by the compressions, and which can be called an inside height. In particular, torso view 182-A has an inside height HS-A, and torso view 182-Z has an inside height HS-Z, respectively. In general, inside heights HS-A and HS-Z are not the same in FIG. 11.

In some embodiments, the top aspect detected by the top height sensor includes a resting height of the patient's chest, which would be H0 at CN0. In such embodiments, target values including the second value can be determined as a fraction of the resting height of the chest at the time. This fraction could be, for example, 20% to 25%.

In some of these instances, the patient may be lying on a flexible support surface. If the surface recedes according to a substantially linear relationship with the force of a compression, then the above relationship may be workable but the percentage may need to be higher.

As mentioned above, a CPR system according to embodiments may or may not be able to determine the resting chest height by itself. Indeed, the top height sensor may be able to determine its own top aspect of its location, but it might not know whether there was displacement underneath the patient without the assistance of a bottom height sensor.

In some embodiments, the top aspect detected by the top height sensor includes a resting height of the patient's chest. In such embodiments, target values including the second value can be determined so that at least some of the compressions reach substantially the same height, measured above the support surface, as previous compressions. An example is now described.

FIG. 12 is a diagram 1202 that repeats aspects of diagrams 202, 204. At CN1, CN2, corresponding torso views 182-B, 182-D are shown. The vertical axis does not plot only the chest resting height, but also the height at the deepest point of the compression. In fact, target depths D1, D2 at CN1, CN2 are superimposed on torso views 182-B, 182-D. In this particular case, the compressions at CN1 and CN2 reach substantially the same height, measured above the support surface. In other words, the inside height reached is the same (HS) for both of these compressions, and possibly others. This is an example of where a target value for the second value is determined so that a second compression D2 that corresponds to CN2 reaches substantially the same height, measured above the support surface, as a compression D1 that corresponds to CN1. A potential risk of this approach is that, if the chest deforms markedly over a long period of compressions, the target depth of individual later compressions could become quite shallow, possibly too shallow to supply adequate blood flow.

In addition to breaking down gradually, the patient's torso may break down in more sudden ways. Embodiments may detect this, and may adjust the target values of the depth variable to account for this. Accordingly, if the torso recedes more suddenly than is suggested in diagram 202, the subsequent few compressions are less likely to be deeper than optimum.

A CPR feedback system according to embodiments, therefore, may include a force detection module, for example within the top height sensor. Such a force detection module can be configured to detect an amount of force that is exerted by the rescuer during one of the compressions. In such embodiments, target values including the above-mentioned second value can be determined at least in part from the detected amount of force. For example, if a sudden additional breakdown is detected that is larger than a previous trend of breakdowns, then subsequent target values may be adjusted so as to not press as deeply as would have been dictated by a profile that had been followed so far. This could also be the type of event that is reported at the bottom of screen 412 in FIG. 4.

There are different types of changes in the force of a compression that may be detected during a rescue session according to embodiments. Detection may operate in terms of the compressions number being CN1 or CURRENT_CN, and the subsequent target values may be determined from the detected amount of force, instead of just a profile that was being followed. These subsequent target values may include what is considered the above-mentioned second value of the target value returned by the depth variable. The entire remainder of the profile may be adjusted accordingly, for example it can be accelerated to a new point, or shifted to a more gradual descent, etc. One more example is to adjust the value of F in equation 1005, so as to effectively adjust the value of DR. Examples of detection are now described.

Figure 13:
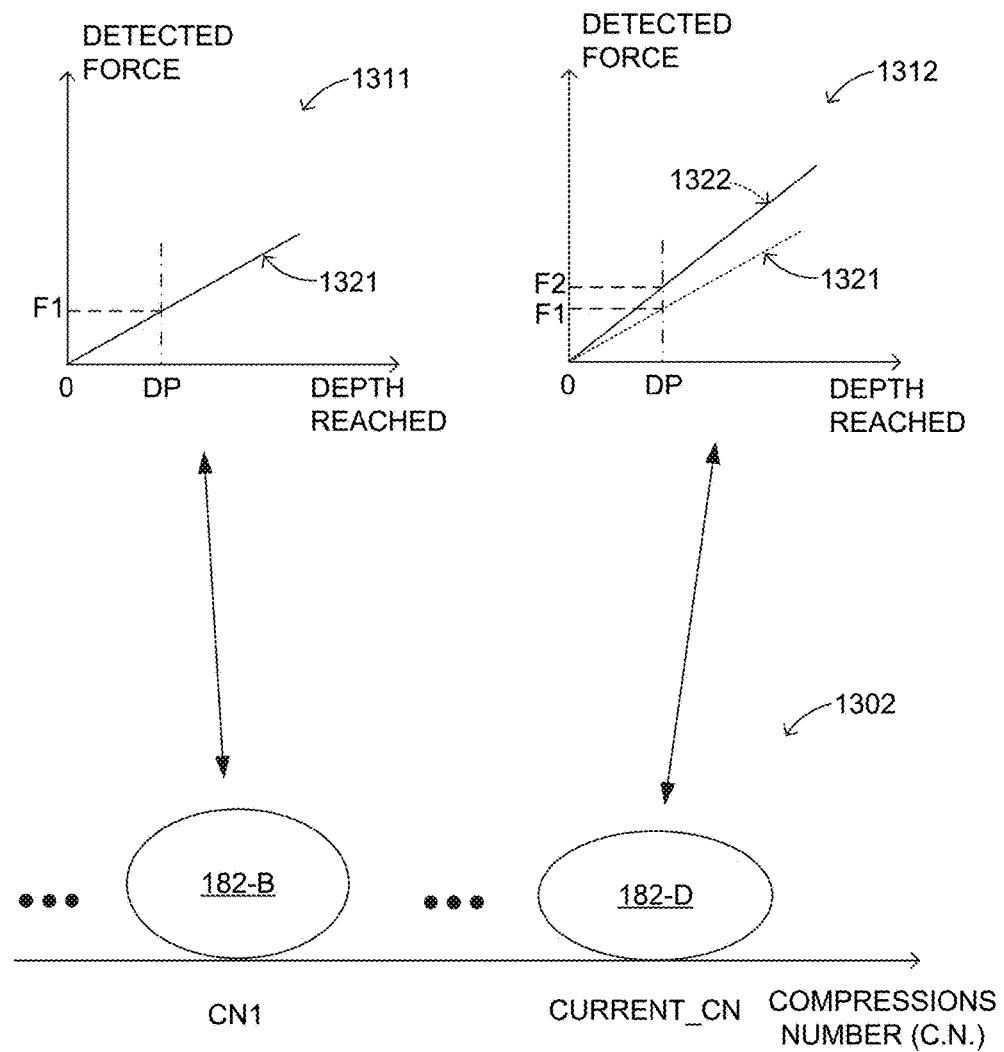
FIG. 13 is a composite diagram illustrating a type of a change in a force of a compression that may be a detected during a rescue session according to embodiments.

FIG. 13 is a composite diagram, which includes a diagram 1302 that repeats aspects of diagram 202 of FIG. 2. FIG. 13 further includes diagrams 1311, 1312, which plot, for compressions numbers CN1 and CURRENT_CN of diagram 1302, the detected force against the depth reached of the corresponding compression.

In diagram 1311, a relationship 1321 is plotted, which in this example is linear. The force F1 detected at a sample depth point DP may be recorded.

In diagram 1312, a relationship 1322 is plotted, similarly with diagram 1311. In addition, relationship 1321 is repeated in diagram 1312, so as to draw the contrast.

In diagram 1312, it may be monitored whether relationship 1322 as a whole becomes substantially different from relationship 1321. Or, force F2 may be detected at the same depth point DP as in diagram 1311. It may be further monitored whether force F2 becomes substantially different from force F1. It may be further observed whether the changes that are being monitored for are gradual or sudden.

FIG. 13 is thus an example where an amount of force is detected while compressing through depth point DP during different compressions at CN1, CURRENT_CN. A good value for depth point DP can be about half the depth of an initial target depth. For example, if the initial target depth is 5 cm-6 cm, then DP could be 3 cm below the initial chest resting height.

In the example of FIG. 13, F2 is larger than F1, reflecting the notion that the chest is stiffening. The opposite may happen, however, if the ribs break. The remainder of the profile for the session can be adjusted accordingly.

In other embodiments of force detection, a non-linearity may be detected in how much force is detected along a travel of a single compression. An example is now described.

Figure 14:
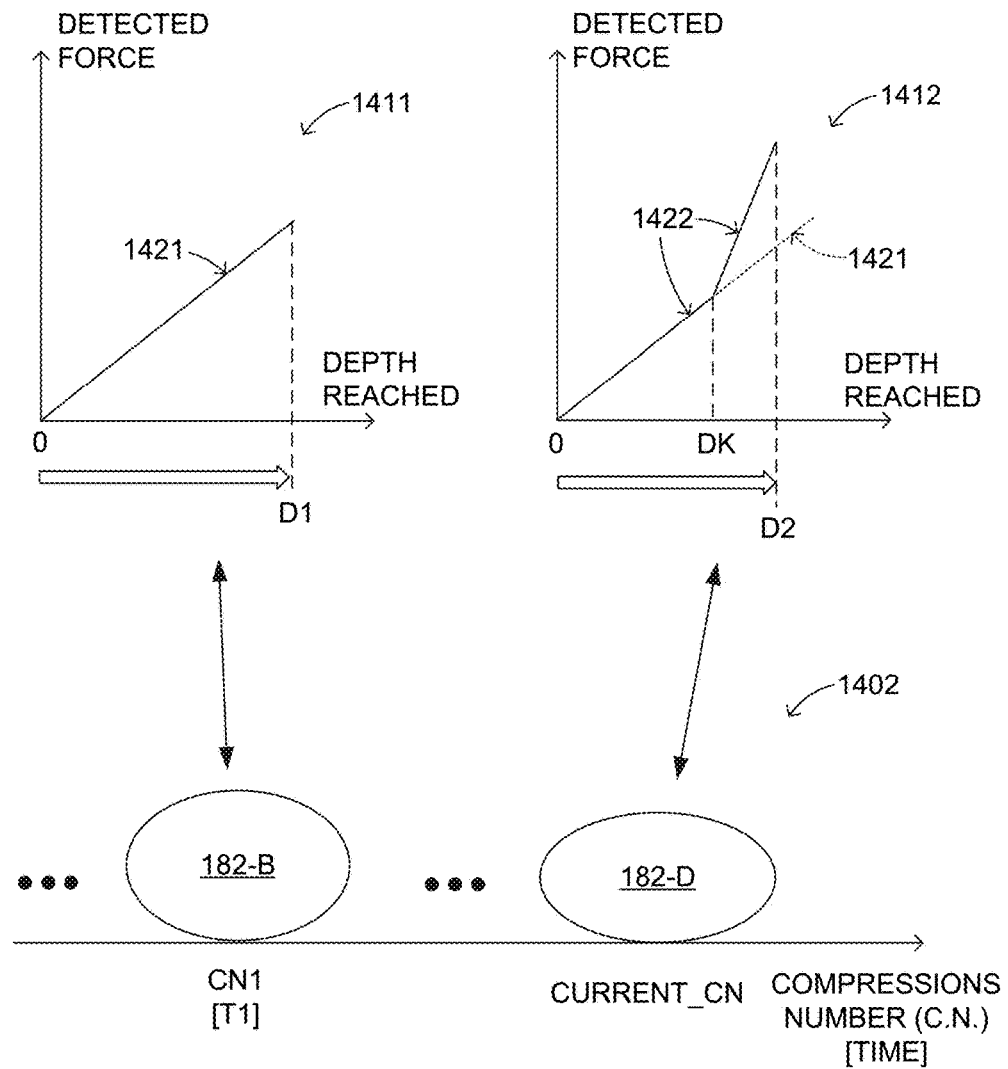
FIG. 14 is a composite diagram illustrating another type of a change in a force of a compression that may be a detected during a rescue session according to embodiments.

FIG. 14 is a composite diagram, which includes a diagram 1402 that is identical to diagram 1302 of FIG. 13. FIG. 14 further includes diagrams 1411, 1412, which plot the detected force against the depth reached for compressions numbers CN1 and CURRENT_CN of diagram 1402.

In diagram 1411, a relationship 1421 is plotted of the force detected along a travel of the compression, which in this example is linear. The full depth reached by the compression, assuming the rescuer is performing exactly as coached, as D1.

In diagram 1412, a similar relationship 1422 is plotted. The full depth reached by the compression, assuming the rescuer is performing exactly as coached, as D2, which can be less than D1. In addition, relationship 1421 is repeated in diagram 1412, so as to draw the contrast.

In diagram 1412, it may be monitored whether relationship 1422 as a whole becomes non-linear, especially in ways that relationship 1421 is not. In this example, relationship 1422 exhibits a "knee" at a depth DK, deeper than which the compression resistance increases substantially. The compression resistance here is the amount of force needed or exerted per unit compression depth along the travel of the compression. In such embodiments, the target values may be adjusted, for example so that subsequent compressions reach only down to knee depth DK, or to a depth determined from knee depth DK.

In the example of FIG. 14, relationship 1421 was linear and relationship 1422 had linear components. The above mentioned concept of the compression resistance, however, need not be confined to situations where the detected force changes linearly with respect to the distance traveled. An example is now described.

Figure 15:
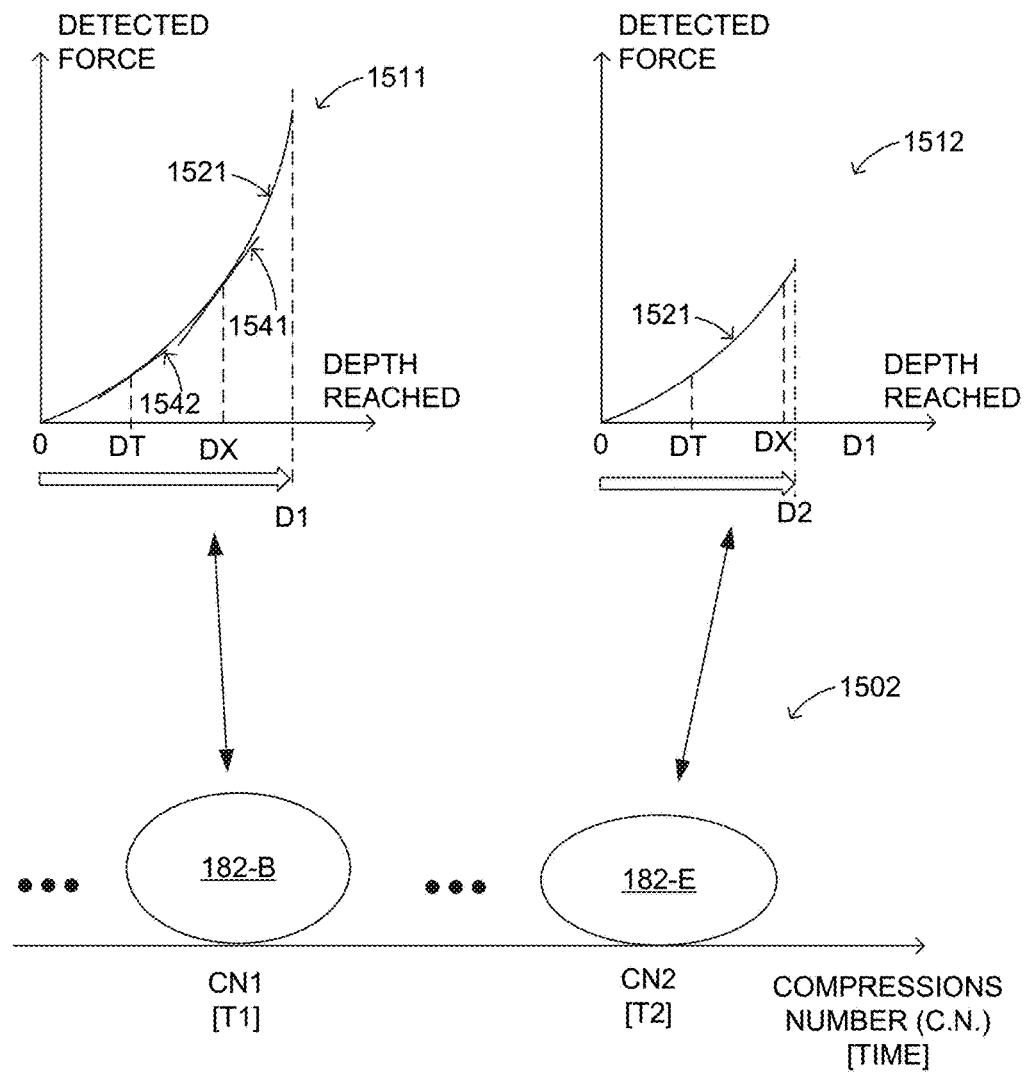
FIG. 15 is a composite diagram illustrating how a change in a detected force of a compression may be used to set a compression depth according to embodiments.

FIG. 15 is a composite diagram, which includes a diagram 1502 that includes aspects of diagram 202 of FIG. 2. FIG. 15 further includes diagrams 1511, 1512, which plot the detected force against the depth reached at C.N.s CN1 and CN2 of diagram 1502.

In diagram 1511, a relationship 1521 is plotted of the force detected along a travel of the compression. The full depth reached by the compression, assuming the rescuer is performing exactly as coached, as D1.

Relationship 1521 is not linear. A compression resistance CR for a certain compression can be defined, for a specific point of the travel of the certain compression, from a derivative of the detected force with respect to the travel. This compression resistance CR can be visualized as a tangent on line 1521. In diagram 1511, the steeper the tangent is, the higher the CR is. Then using the force detected by the module at different points in the downward travel of the certain compression, the compression resistance can be computed for various points in the travel. A residual depth DX can be then determined within the travel, in which the compression resistance CR for points in the travel deeper than the residual depth becomes higher than a threshold compression resistance CRT. The tangent at residual depth DX is visualized by tangent line 1541.

Then target values can be set so that subsequent compressions reach a final depth that is determined by residual depth DX, or substantially equals residual depth DX. In the example of FIG. 15, this is shown in diagram 1512, where the final depth reached by a subsequent compression is D2, assuming the rescuer is performing exactly as coached. D2 is slightly larger than the determined residual depth DX. These target values may include the above-mentioned second value of the target value returned by the depth variable, so that a second one of the compressions, which corresponds to the compressions number having the second value, reaches the final depth.

Embodiments that use the compression resistance this way to determine a final depth can be the compressions at any part of the session. In addition, they could be the first few compressions, in which case the initial depth of the CPR feedback system might not need to be initialized for the patient, regardless of the type of patient. In such embodiments, however, the setting of the threshold compression resistance may have to take into account resistance at points of the travel of the compression other than the early shallow points. This will be useful for an instance where a patient has a very muscular chest, causing the compressions resistance to start at an already high value, while compressions should progress deeper. In such embodiments, the residual depth can be defined such that the threshold compression resistance CRT is at least 20% higher for the residual depth DX than for a test point DT within the travel. In embodiments, DT is set as a fraction of DX. In the example of FIG. 15, DT is one-half of DX. At point DT the tangent to relationship 1521 is shown by a tangent line 1542. Tangent line 1541 is at least 20% steeper than tangent line 1542.

Of course, embodiments include combining one or more of the above mentioned approaches. In addition, values detected and generated from the event may be recorded for later analysis.

In a CPR feedback system according to embodiments, the memory may be non-volatile, and operate by receiving electrical power. In addition, while a CPR rescue session proceeds, the depth variable might not lose its target value, even if there is power interruption, for example by the system being inadvertently turned off. An example is now described.

Figure 16:
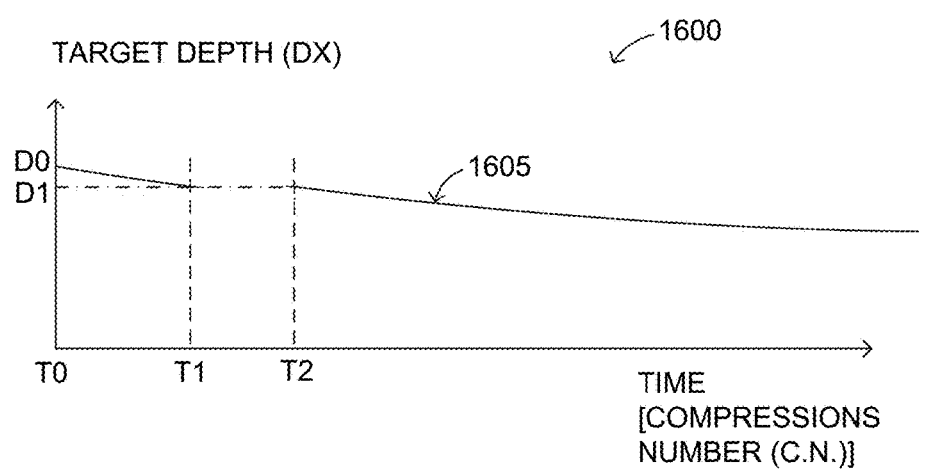
FIG. 16 is a time diagram showing how a brief power interruption might not cause loss of the current depth profile during a rescue session according to embodiments.

FIG. 16 is a diagram 1600 whose horizontal axis is time that incorporates a compressions number, as seen in FIG. 3. In diagram 1600, the vertical axis is for target values of depth variable DX. These values are plotted as a profile 1605 where, however, time T1 is a power loss moment at which the memory stops receiving electrical power. At time T1, the target value is a first value D1. Time T2 comes later than power loss moment T1, and possibly at least 4 sec after T1. When the memory restarts receiving electrical power at T2, then the next target value can be derived from the first value D1, and even be first value D1. Accordingly, even if power is briefly lost, the place in the profile need not be lost according to embodiments.

The above can be true for even longer power interruptions. It need not, however, be true for interruptions longer than one hour, because the same rescue session would have ended by then.

Embodiments also include user interfaces with screens that variously deal with the question of the target values shifting over time. In some embodiments, the aforementioned indication that is perceptible by the rescuer includes a graphic depiction displayed on the screen. The graphic depiction can be of the current value, which is the target value for the current compression. In some of these embodiments, the graphic depiction does not shift within the screen, within the time the C.N. has transitioned from having the first value to having the second value. In other embodiments, the graphic depiction has shifted, as seen in the example below.

Figure 17:
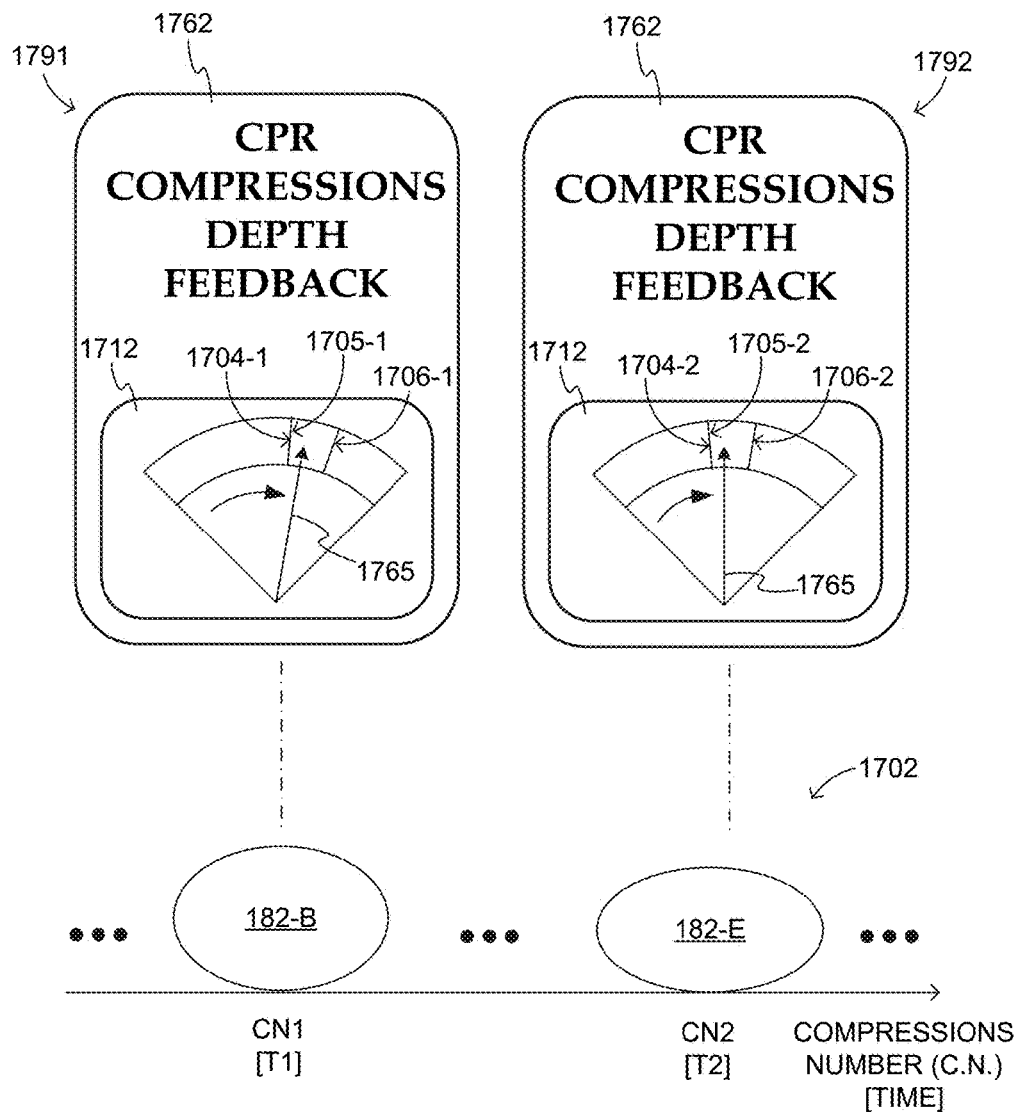
FIG. 17 is a composite diagram showing how a user interface with a screen displays a visual indication that provides feedback to a rescuer performing CPR compressions, and the visual indication shifts according to embodiments.

FIG. 17 is a composite diagram, which includes a diagram 1702 that is identical to diagram 1502 of FIG. 15. FIG. 17 further includes views 1791, 1792 at CN1, CN2, of a sample user interface of a system according to embodiments. The user interface has a frame 1762 with writings as shown, and a screen 1712 within frame 1762.

In both views 1791, 1792, the aforementioned indication that is perceptible by the rescuer includes a graphic depiction of the target compression depth. In the particular example of FIG. 17, the target compression depth is shown as a range. In view 1791, the range has a lower limit 1704-1 and an upper limit 1706-1. In this example, the target value may be considered to be 1705-1, which coincides with lower limit 1704-1. In view 1792, the range has a lower limit 1704-2 and an upper limit 1706-2. The target value may then be considered to be 1705-2, which coincides with lower limit 1704-2.

For screen 1712, the actual compression depth is depicted in real time by an arrow 1765 that rotates to the right in proportion to the depth reached, as a gauge or a dial. The rotation of arrow 1765 is depicted by a curved arrow. In both views 1791, 1792, arrow 1765 meets target values 1705-1, 1705-2. The compression in view 1792 is less, however, because the graphic depiction has shifted; indeed, the depictions of 1704-2, 1705-2 and 1706-2 have shifted to the left with respect to frame 1762, from the earlier corresponding depictions of 1704-1, 1705-1 and 1706-1, commensurately with the diminished target values.

It is preferred that the rescuer has been trained as to the target depths diminishing over time. Accordingly, the rescuer will not be surprised as the depictions shift, and will not continue to reset the system to the initial depth, perhaps concerned that the system is malfunctioning.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document.

Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 18:
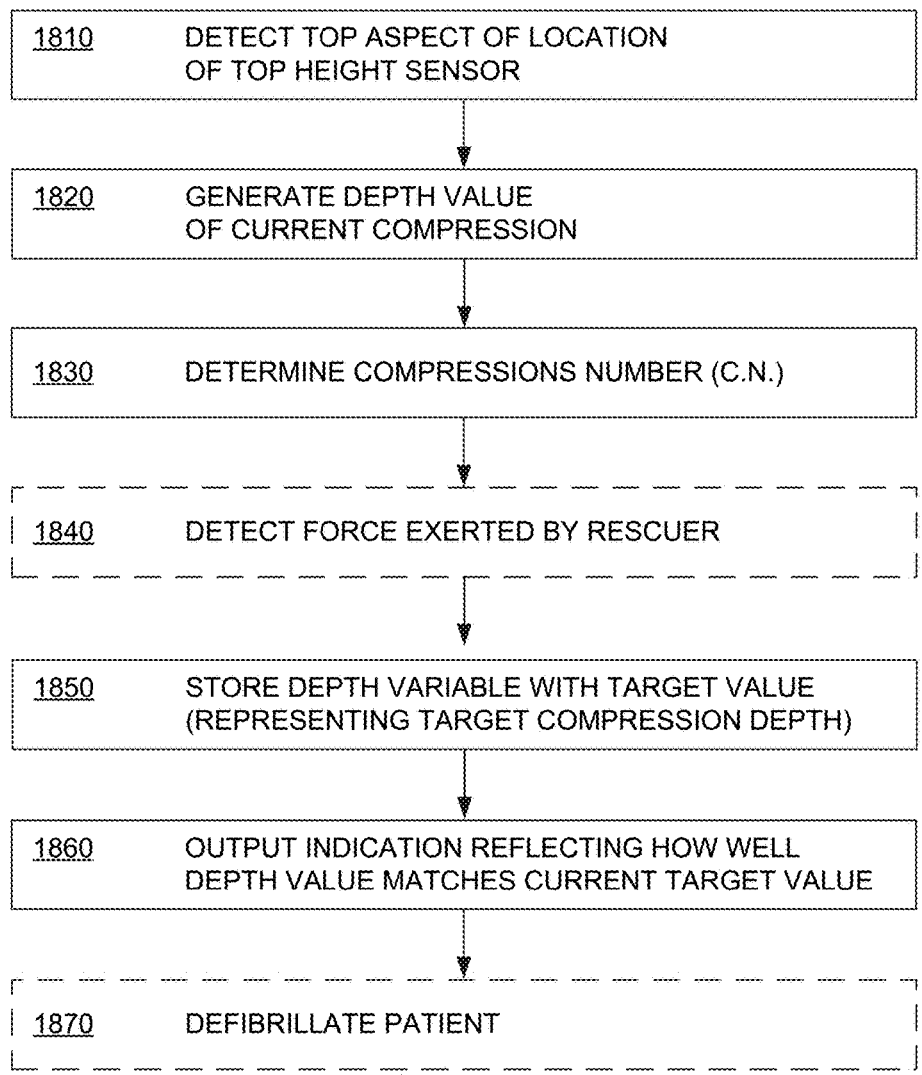
FIG. 18 is a flowchart for illustrating methods according to embodiments.

FIG. 18 shows a flowchart 1800 for describing methods according to embodiments. The methods of flowchart 1800 may also be practiced by embodiments described elsewhere in this document, such as a CPR feedback system that includes a top height sensor, a depth module, a counter, a memory and a user interface that has an output device.

According to an operation 1810, a top aspect of a location of a top height sensor can be detected.

According to another operation 1820, a depth value may be generated via the depth module, from the detected top aspect. The depth value can be related to a detected depth that is reached by at least a current one of the compressions.

According to another operation 1830, a compressions number (C.N.) may be determined, via the counter and from the detected top aspect. The C.N. can be related to a number of the compressions that have been performed during the session, for example the number of the compressions that have been performed so far.

According to another, optional operation 1840, an amount of force can be detected, for example using an additional force detection module of the system. The detected force can be the force exerted by the rescuer during a first compression, which corresponds to the C.N. having a first value.

According to another operation 1850, a depth variable can be stored in the memory. The depth variable may represent a target depth for the compressions. The depth variable can be configured to return a target value that depends on the determined compressions number. This target value can be (a) a first value for one of the C.N.s that corresponds to the above-mentioned first compression (e.g. CN1), (b) a current value for a C.N. that corresponds to a current compression, (c) a second value for another of the C.N.s that is larger by at most 100 than the one of the compressions numbers that corresponds to the first compression (e.g. CN2), etc.

The second value can be at least 4% smaller than the first value. In some embodiments, the second value is determined at least in part from a preset profile that depends on the determined compressions number. In some embodiments, if at operation 1840 an amount of force has been detected, the second value may be determined at least in part from the detected amount of force.

According to another operation 1860, an indication may be output via the output device, and responsive to the generated depth value. The indication can be perceptible by the rescuer, and reflect how well the depth value matched the current value.

According to another, optional operation 1870, the patient may be defibrillated by an additional defibrillation module of the system.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Reference numerals are used consistently for the specification and the accompanying drawings, but the values of variables are not necessarily the same across various examples. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

What is claimed is:

1. A system comprising:
   a counter configured to determine, based at least in part on
      a first signal from a sensor representative of chest compressions being applied to a patient at a first time period, a first number related to a number of applied chest compressions during the first time period, and, based at least in part on a second signal from the sensor representative of chest compressions being applied to the patient at a second time period, a second number related to a number of applied chest compressions during the second time period;

a processor; and at least one memory including a computer program code, the at least one memory and the computer program code configured to cause the processor:

to compute, based at least in part on the first number related to the number of applied chest compressions during the first time period, a first target depth value; and to compute, based at least in part on the second number related to the number of applied chest compressions during the second time period, a second target depth value, wherein the second target depth value is different from the first target depth value.

2. The system of claim 1, further comprising a depth module for generating a first detected depth value based at least in part on the first signal and a second detected depth value based at least in part on the second signal.

3. The system of claim 2, further comprising an output device for outputting the first detected depth value and the first target depth value at the first time period and outputting the second detected depth value and the second target depth value at the second time period.

4. The system of claim 3, wherein the output device includes a screen, wherein the screen displays the first target depth value at the first time period and the screen displays the second target depth value at the second time period.

5. The system of claim 1, wherein the sensor is configured to be maintained at a substantially vertical relationship with respect to a top of the patient's chest.

6. The system of claim 1, wherein the memory stores a maximum decrease in depth value, wherein the difference between the first target depth value and the second target depth value is not more than the maximum decrease in depth value.

7. The system of claim 1, wherein the first target depth value includes a first target depth value range and the second target depth value includes a second target depth value range, further wherein the second target depth value range is different from the first target depth value range.

8. The system of claim 1, wherein the memory stores a lookup table and the first target depth value and the second target depth value are determined based at least in part on the lookup table.

9. The system of claim 1, wherein the memory stores an initial target depth value, the initial target depth value being greater than the first target depth value and the second target depth value.

10. The system of claim 1, wherein the second target depth value is less than the first target depth value.

11. A method for assisting a rescuer to perform Cardio-Pulmonary Resuscitation ("CPR") compressions on a chest of a patient by using a CPR feedback system that includes a processor, a counter, and a sensor, the method comprising:

determining by the counter of the CPR feedback system, based at least in part on a first signal from a sensor representative of chest compressions being applied to the patient at a first time period, a first number related to a number of applied chest compressions during the first time period;

determining by the counter, based at least in part on a second signal from the sensor representative of chest compressions being applied to the patient at a second time period, a second number related to a number of applied chest compressions during the second time period;

at the first time period, computing by the processor of the CPR feedback system, based at least in part on the first number related to the number of applied chest compressions during the first time period, a first target depth value; and at the second time period, computing by the processor, based at least in part on the second number related to the number of applied chest compressions during the second time period, a second target depth value, wherein the second target depth value is different from the first target depth value.

12. The method of claim 11, further comprising generating by a depth module a first detected depth value based at least in part on the first signal and a second detected depth value based at least in part on the second signal.

13. The method of claim 12, further comprising outputting on a screen the first detected depth value and the first target depth value at the first time period and outputting on the screen the second detected depth value and the second target depth value at the second time period.

14. The method of claim 11, further comprising:

detecting by the sensor the first signal representative of chest compressions being applied to the patient at the first time period; and detecting by the sensor the second signal representative of chest compressions being applied to the patient at the second time period.

15. The method of claim 11, further comprising storing in a memory a maximum decrease in depth value, wherein the difference between the first target depth value and the second target depth value is not more than the maximum decrease in depth value.

16. The method of claim 11, wherein the first target depth value includes a first target depth value range and the second target depth value includes a second target depth value range, further wherein the second target depth value range is different from the first target depth value range.

17. The method of claim 11, further comprising storing in a memory a lookup table, wherein the first target depth value and the second target depth value are determined based at least in part on the lookup table.

18. The method of claim 11, further comprising storing in a memory an initial target depth value, wherein the initial target depth value is greater than the first target depth value and the second target depth value.

19. The method of claim 11, wherein the second target depth value is less than the first target depth value.

* * * * *